US011772831B2

(12) United States Patent
Stroup

(10) Patent No.: US 11,772,831 B2
(45) Date of Patent: Oct. 3, 2023

(54) VACUUM-CONTROLLED LIQUID DELIVERY SYSTEMS AND METHODS FOR DRAWING LIQUID INTO CONTAINERS

(71) Applicant: David K. Stroup, Boise, ID (US)

(72) Inventor: David K. Stroup, Boise, ID (US)

( * ) Notice: Subject to any disclaimer, the term of this patent is extended or adjusted under 35 U.S.C. 154(b) by 0 days.

(21) Appl. No.: 17/963,051

(22) Filed: Oct. 10, 2022

(65) Prior Publication Data

US 2023/0036574 A1 Feb. 2, 2023

Related U.S. Application Data

(62) Division of application No. 17/051,752, filed as application No. PCT/US2019/035232 on Jun. 3, 2019.

(60) Provisional application No. 62/680,293, filed on Jun. 4, 2018.

(51) Int. Cl.
| | |
|---|---|
| *B65B 3/00* | (2006.01) |
| *B65B 3/14* | (2006.01) |
| *A61M 5/178* | (2006.01) |
| *A61M 5/31* | (2006.01) |
| *B65B 31/02* | (2006.01) |

(52) U.S. Cl.
CPC ........... *B65B 3/003* (2013.01); *A61M 5/1782* (2013.01); *B65B 3/14* (2013.01); *A61M 2005/3114* (2013.01); *B65B 31/02* (2013.01)

(58) Field of Classification Search
CPC .......... B65B 3/003; B65B 31/02; B65B 3/04; A61M 5/1782; A61M 2005/3114; A61J 1/2096; A61J 1/1406
USPC ........................................................ 53/396
See application file for complete search history.

(56) References Cited

U.S. PATENT DOCUMENTS

| | | | | |
|---|---|---|---|---|
| 2,503,147 | A * | 4/1950 | Applezweig | B65B 3/003 141/181 |
| 3,982,539 | A * | 9/1976 | Muriot | A61M 1/71 604/245 |
| 4,252,159 | A * | 2/1981 | Maki | A61J 1/2096 141/95 |
| 5,884,457 | A | 3/1999 | Ortiz | |
| 5,911,252 | A | 6/1999 | Cassel | |
| 8,037,659 | B2 * | 10/2011 | Osborne | A61J 1/2096 53/53 |
| 8,172,795 | B2 * | 5/2012 | Lum | A61M 5/31511 604/125 |
| 8,347,925 | B2 | 1/2013 | Li | |
| 8,887,770 | B1 | 11/2014 | Shippert | |

(Continued)

OTHER PUBLICATIONS

PCT/US2019/035232 International Search Report and Written Opinion dated Aug. 9, 2019.

*Primary Examiner* — Timothy P. Kelly
*Assistant Examiner* — Stephanie A Shrieves
(74) *Attorney, Agent, or Firm* — Wagenknecht IP Law Group PC

(57) ABSTRACT

A vacuum controlled liquid delivery system, including a primary chamber; a manifold assembly affixed to the primary chamber, the manifold assembly comprising a feed line and an external pressure line; and a cap configured to reversibly engage the manifold assembly at one end and reversibly cap a syringe at another end, the cap comprising a septum and a porous plug, wherein when the cap is attached to the manifold assembly the feed line passes through the septum, and further wherein the porous plug seals upon contact with a liquid.

9 Claims, 13 Drawing Sheets

(56) References Cited

U.S. PATENT DOCUMENTS

| | | |
|---|---|---|
| 2007/0186992 A1 | 8/2007 | Bullen |
| 2012/0029428 A1 | 2/2012 | Neer |
| 2012/0157914 A1 | 6/2012 | Stroup |
| 2013/0085466 A1* | 4/2013 | Ishiwata .............. B65D 51/002 604/403 |
| 2013/0220484 A1 | 8/2013 | De Marco |
| 2014/0263147 A1 | 9/2014 | Py |
| 2015/0290079 A1* | 10/2015 | Nishioka ............... A61J 1/2096 141/2 |
| 2015/0292495 A1 | 10/2015 | Sweeney |
| 2015/0321780 A1* | 11/2015 | Py ........................... B65B 43/54 141/1 |
| 2016/0151570 A1 | 6/2016 | Rhinehart et al. |
| 2016/0243839 A1 | 8/2016 | Ikushima |
| 2016/0340066 A1 | 11/2016 | Perazzo |
| 2017/0172848 A1* | 6/2017 | Goodman ........... B01F 35/7174 |
| 2017/0312543 A1 | 11/2017 | Franci |

\* cited by examiner

24

TO FLUID PATH

FROM FLUID SOURCE

*(CONDITION: ON, PATH 1)*

TO ATMOSPHERE

FROM FLUID SOURCE

*(CONDITION: ON, PATH 2)*

VACUUM-CONTROLLED LIQUID DELIVERY SYSTEMS AND METHODS FOR DRAWING LIQUID INTO CONTAINERS

CROSS REFERENCE TO RELATED APPLICATIONS

This is a divisional of U.S. patent application Ser. No. 17/051,752, filed Oct. 29, 2020, which is a US national phase of international patent application PCT/US2019/035232 filed Jun. 3, 2019, which claims benefit of priority to U.S. provisional patent application No. 62/680,293, filed Jun. 4, 2018; the entire content of each is herein incorporated by reference in its entirety.

TECHNICAL FIELD

The invention relates to systems and methods for loading containers and more specifically to vacuum controlled systems and methods for drawing a liquid into a container.

BACKGROUND OF THE INVENTION

Disposable syringes are widely used to administer medications in hospitals and in medical research environments. To load a syringe, the medical worker typically grasps the barrel with one hand and the plunger with another. In some instances, the hand holding the barrel also holds a medication bottle while the plunger is pulled. This action can be repeated numerous times throughout the day, and thus week and year. The repetition of grasping and pulling motions places the worker at risk of repetitive motion injury, such as carpal tunnel syndrome.

Carpal tunnel syndrome is a painful progressive condition caused by the compression of a key nerve in the wrist, the median nerve. This nerve, which controls the sensations and nerve impulses for much of the hand, passes through a narrow passageway of the ligament and bones called the carpal tunnel. When swelling causes the median nerve to be compressed in the tunnel, numbness, tingling, and pain can result.

In addition to risk of repetitive motion injury, repeatedly loading syringes with medications also exposes the worker to needle sticks and toxic medications. Accordingly, there is a need to develop automated processes for loading syringes for worker safety.

SUMMARY OF THE INVENTION

The invention provides improved systems and methods for drawing a liquid into a syringe, which decreases exposure of potentially toxic medications to workers, and decreases the risk of injury from repetitive motions. In particular, a vacuum controlled liquid delivery system is provided, which includes a receiving chamber configured to house an expandable container, such as a syringe or bag, during expansion; and a fitting train in fluid communication with a liquid feed line, where the fitting train regulates passage of liquid into the receiving chamber for delivery into a received container. The chamber seals air-tight to permit operation of the system by applying vacuum forces through suitable lines, valves and pumps.

The fitting train includes a pair of detachable valves that selectively permit and prevent liquid delivery across the train when attached and when detached maintain a liquid-tight seal. As such, a filled syringe removed from the fitting train preferably remains capped by one of the valves from the valve pair. In preferred embodiments, one of the valves within the pair of valves controls the opening and closing of both valves within the pair of valves so that they do not have to be independently opened and closed. Exemplary valves used in combination can include a luer valve, a spike valve, and a valve having an inner housing configured for longitudinal movement in relation to an outer housing to open and close the valve.

The system is operated by actuating a set of in-line control valves by way of a control module. Thus, the system includes executable software loaded in a computer or downloadable to a computer that instructs the opening and closing of control valves to fill an expandable container with liquid. Exemplary control valves can include a feed valve that regulates liquid delivery to the fitting train, a chamber vacuum valve that regulates vacuum inside the chamber, and a feed line vacuum valve that regulates vacuum inside the feed line. The vacuum can be monitored by one or more a vacuum meters configured to measure vacuum within the chamber and/or the feed line.

An exemplary operation of the vacuum controlled liquid delivery system, can include connecting the feed line of the system to a feed tank which includes a liquid for delivery, mounting a container to the fitting train so that the fitting train is in an open position; forming an air-tight seal within the receiving chamber; inducing a vacuum in the receiving chamber and in the feed line; opening the feed line to fill the expandable container with the liquid under the vacuum forces; closing the feed line valve; relieving the vacuum from the receiving chamber; closing the pair of detachable valves; and removing the container from the receiving chamber.

In another exemplary configuration, a vacuum controlled liquid delivery system is provided, which includes a receiving chamber sized to house an expandable container during its expansion; a manifold assembly accessing an interior of the chamber, the manifold assembly having a feed line and a manifold vacuum line, where the feed line is configured to feed liquid, and the manifold vacuum line is functionally coupled to a vacuum pump to regulate a vacuum within the manifold assembly; and a cap configured to reversibly engage the manifold assembly to form an air-tight seal and configured to cap an expandable container, the cap including a septum and a porous plug. When the cap is attached to the manifold assembly the feed line passes through the septum to permit passage of liquid. When the porous plug is contacted with the liquid, such as liquid medication, it seals to prevent or reduced spilling into the manifold assembly.

Similarly, the chamber is operably connected to a vacuum pump so that the chamber can held under vacuum. Evacuating air from a closed volume develops a pressure differential between the volume and the surrounding atmosphere. In some embodiments the chamber also has a barrier in alignment but spaced from the manifold assembly to limit displacement of a syringe plunger during syringe filling.

Preferably, the feed line has a non-coring needle for passing through the septum, which can be formed from materials such as silicone or other polymers. During operation the feed line is fluidly connected to a fluid tank, such as a reservoir housing a medication, for delivery across the septum of the cap. The feed line can also include an in-line feed valve that regulates the flow of liquid through the feed line.

A manifold vacuum line is used to adjust the pressure within the manifold assembly and can be operably connected to a vacuum pump that lowers and maintains a lowered pressure within the manifold assembly. The lowered pressure can also be released by way of the manifold vacuum line by a 3-way in-line valve to permit the interior of the manifold assembly to return to ambient or atmospheric pressure, such as during engagement and disengagement of the cap or a capped syringe. When fully engaged, the cap and manifold assembly form an air-tight seal. In some embodiments, the manifold assembly or cap includes an O-ring to form the air-tight seal.

The cap can be engaged with the manifold assembly via friction fit and/or complementary engaging surfaces that mate with one another, which includes various twist lock embodiments, tongue and groove embodiments and others. At another end, the cap preferably caps a storage container for receiving liquid, such as a syringe, via a complementary fitting, such as a luer lock fitting.

When the cap is fully engaged the porous plug is exposed to both the interior of the manifold assembly and the interior of the cap. The porous plug regulates communication between the interior of the manifold assembly and the interior of the cap. Preferably, the porous plug includes an aperture and a swellable matrix that swells to seal the aperture when contacting liquid, such as the medication filling the syringe. In some embodiments the porous plug includes a sucrose material that swells to seal the aperture when contacting liquid. In other embodiments, the porous plug includes a hydrogel that swells to seal the aperture when contacting liquid. In other embodiments, the porous plug includes polymer that swells or polymerizes to seal the aperture when contacting liquid.

Another exemplary operation of the vacuum controlled liquid delivery system, can include connecting the feed line of the system to a feed tank having a liquid, such as a medication, for delivery; capping a collapsible container with the cap; engaging the capped container with the manifold assembly such that an interior of the cap forms an air-tight seal with an interior of the manifold assembly, and the fluid line passes through the septum to fluidly access the container; inducing a vacuum in the receiving chamber and in the manifold assembly; unsealing the fluid feed line to feed the liquid into the container under vacuum and against the porous plug, thereby sealing the plug; resealing the feed line to obstruct flow through the feed line; relieving the vacuum from the receiving chamber and the manifold assembly; and disengaging the capped syringe from the manifold assembly.

BRIEF DESCRIPTION OF THE DRAWINGS

Embodiments of the invention can be better understood with reference to the following drawings, which are part of the specification and represent preferred embodiments. The components in the drawings are not necessarily to scale, emphasis instead being placed upon illustrating the principles of the invention. And, in the drawings, like reference numerals designate corresponding parts throughout the several views.

DETAILED DESCRIPTION OF PREFERRED EMBODIMENTS

The invention provides vacuum-controlled, liquid delivery systems and methods of use. For clarity of disclosure, and not by way of limitation, the invention is discussed according to different detailed embodiments; however, the skilled artisan will recognize that features of one embodiment can be combined with other embodiments and is therefore within the intended scope of the invention.

Among the benefits of the invention include the rapid and automated delivery of liquids into a plurality of containers. Though non-limiting, the invention is particularly useful in medical research and clinical environments, by providing the efficient loading of medical bags and syringes with liquids, such as medications. Accordingly, the systems and methods decrease exposure to potentially toxic medications to workers and decrease risk of injury from repetitive motions.

The skilled artisan will appreciate that the systems and methods disclosed herein can be used with a variety of treatments where administration of a liquid is desired. Among these include administration of pharmaceuticals or nutritional supplements, and saline for hydration.

Figure 1:
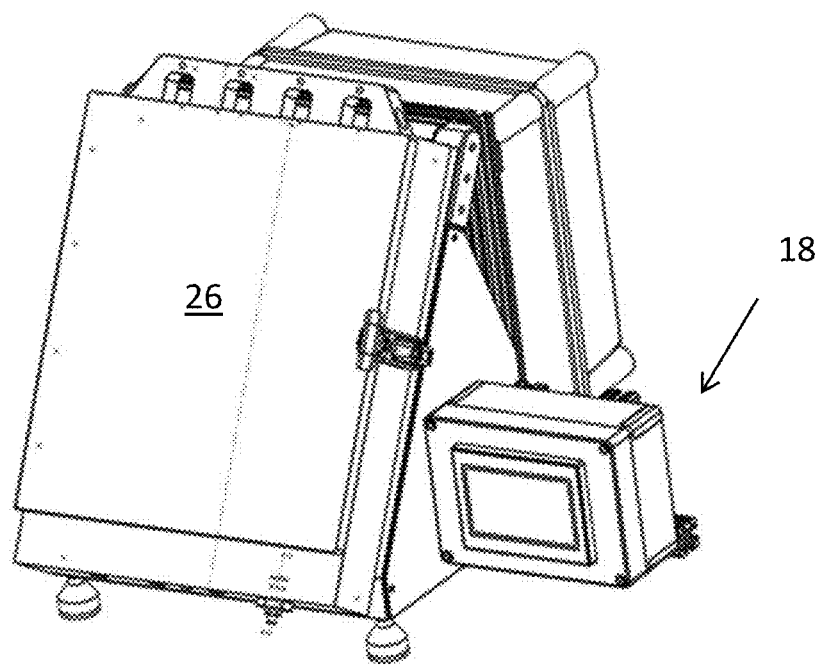
FIG. 1 depicts an exemplary vacuum-controlled liquid delivery system 10.
Figure 2:
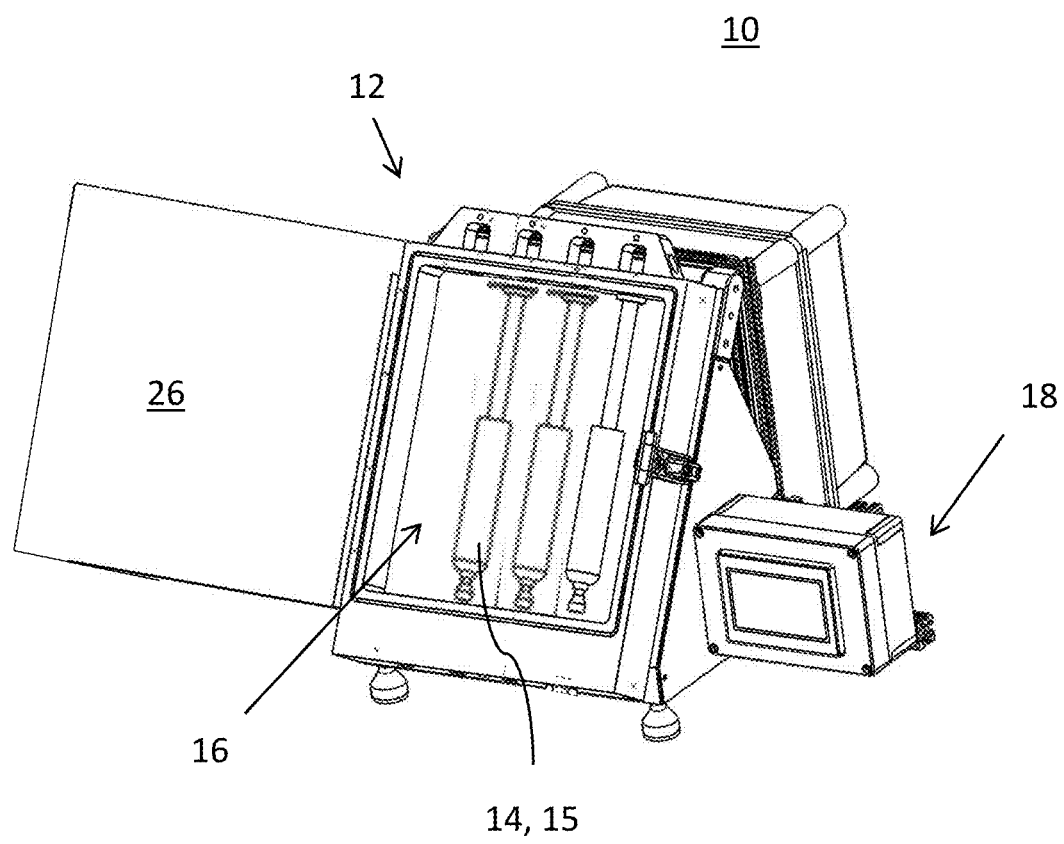
FIG. 2 depicts the system 10 of FIG. 1., with the chamber door 26 open to show the internal chamber 12.
Figure 3:
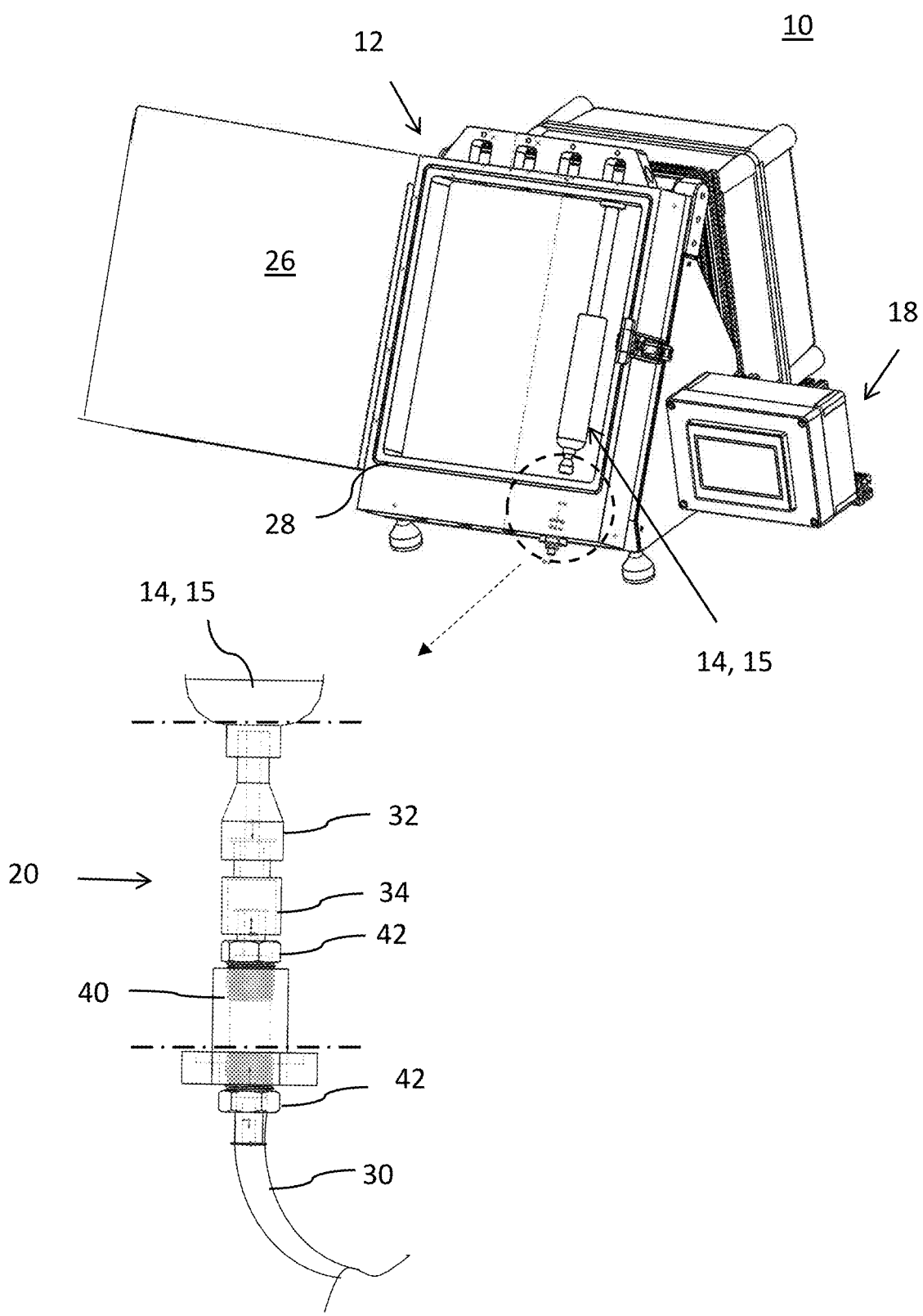
FIG. 3 depicts an exemplary fitting train 20 for regulating liquid flow into a syringe 15.

Beginning now at FIGS. 1-3, the invention provides a vacuum controlled liquid delivery system 10, which includes a receiving chamber 12 configured to house one or more expandable containers 14 for filling. In some embodiments, the receiving chamber 12 houses one or more syringes 15. In other embodiments, the receiving chamber 12 houses one or more expandable bags (not shown). While syringes 15 are typically expandable by way of a movable plunger, expandable bags are typically expandable by unfolding. The artisan will appreciate that syringes 15 can be of any volume, such as, but not limited to less than 1 mL, 1 mL, 5 mL, 10 mL, 25 mL, 50 mL, and more than 50 mL. Though nonlimiting, containers 14 greater than about 100 mL are more frequently provided in the form of an expandable bag, akin to IV bags used during medical treatment. One of ordinary skill in the art will appreciate that, like the syringes 15, bags can be of any size, such as, but not limited to less than 50 mL, 100 mL, 250 mL, 500 mL, 1000 mL, and more than 1000 mL. As such, the dimensions of the receiving chamber 12 can vary depending on the size and number of containers 14 that are to be filled with the liquid.

In view of the above, FIG. 2 depicts an exemplary delivery system 10 with three syringes 15 filled with a medication, with one slot 16 available for a fourth syringe 15. While three syringes 15 are shown, the system 10 can be configured for delivering liquid to as few as one syringe 15 and by altering the size of the chamber 12, many more than four syringes 15.

In some embodiments the user inputs the number and volume of containers 14 into the control module 18. In other embodiments, inserting containers 14 into the chamber 12, such as against a fitting train 20 detects the presence of the container 14, such as by an optical detector (not shown), and notifies the control module 18 to prompt the use for any additional information needed or desired. Accordingly, in some embodiments, the user may be prompted to enter or confirm a container 14 volume and/or configuration. Naturally, technologies such as bar code readers cold be adapted to enter and communicate information about the particular container 14 and liquid.

Figure 4:
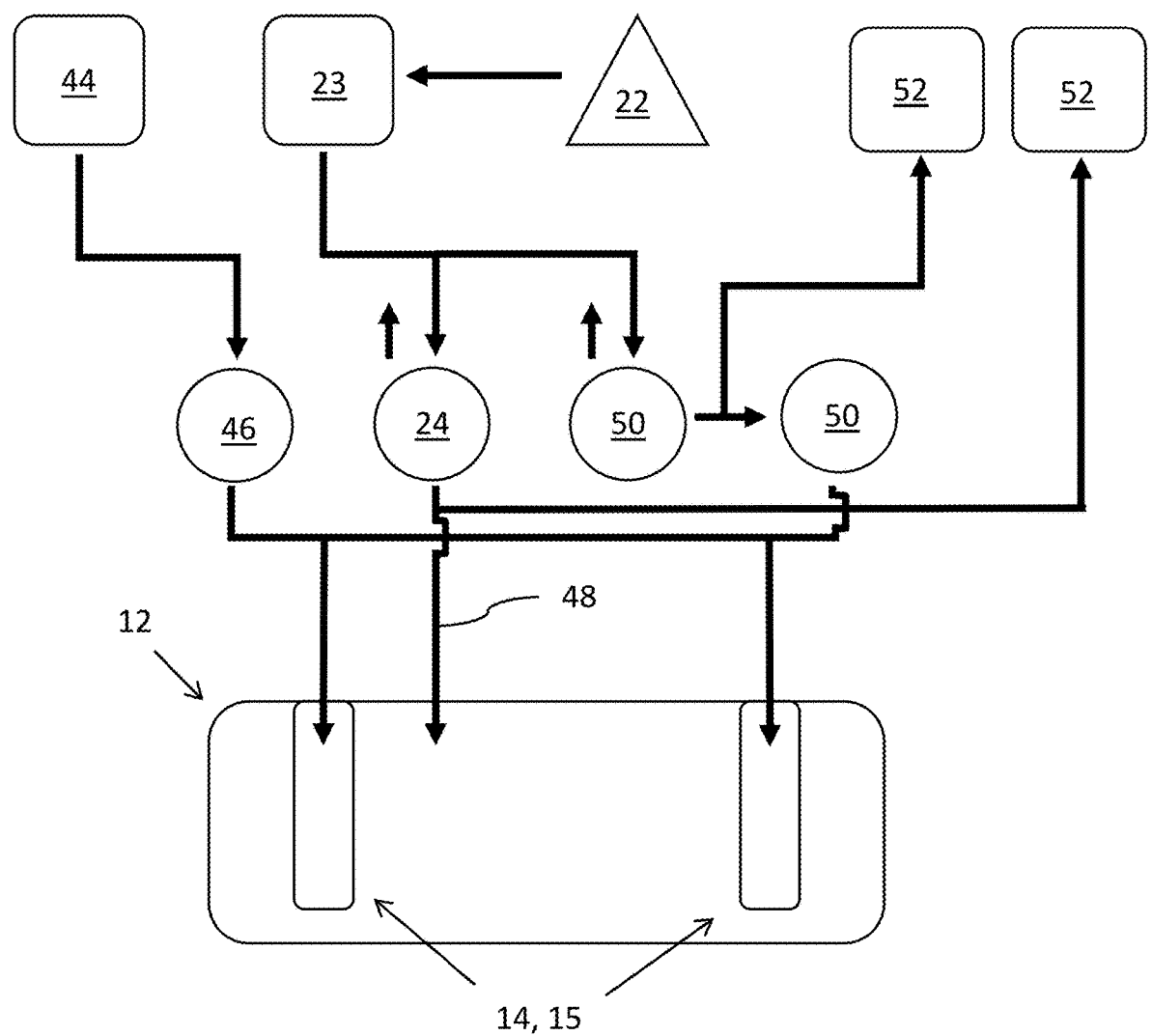
FIG. 4 depicts an exemplary schematic of the operation of the system 10.
Figure 7:
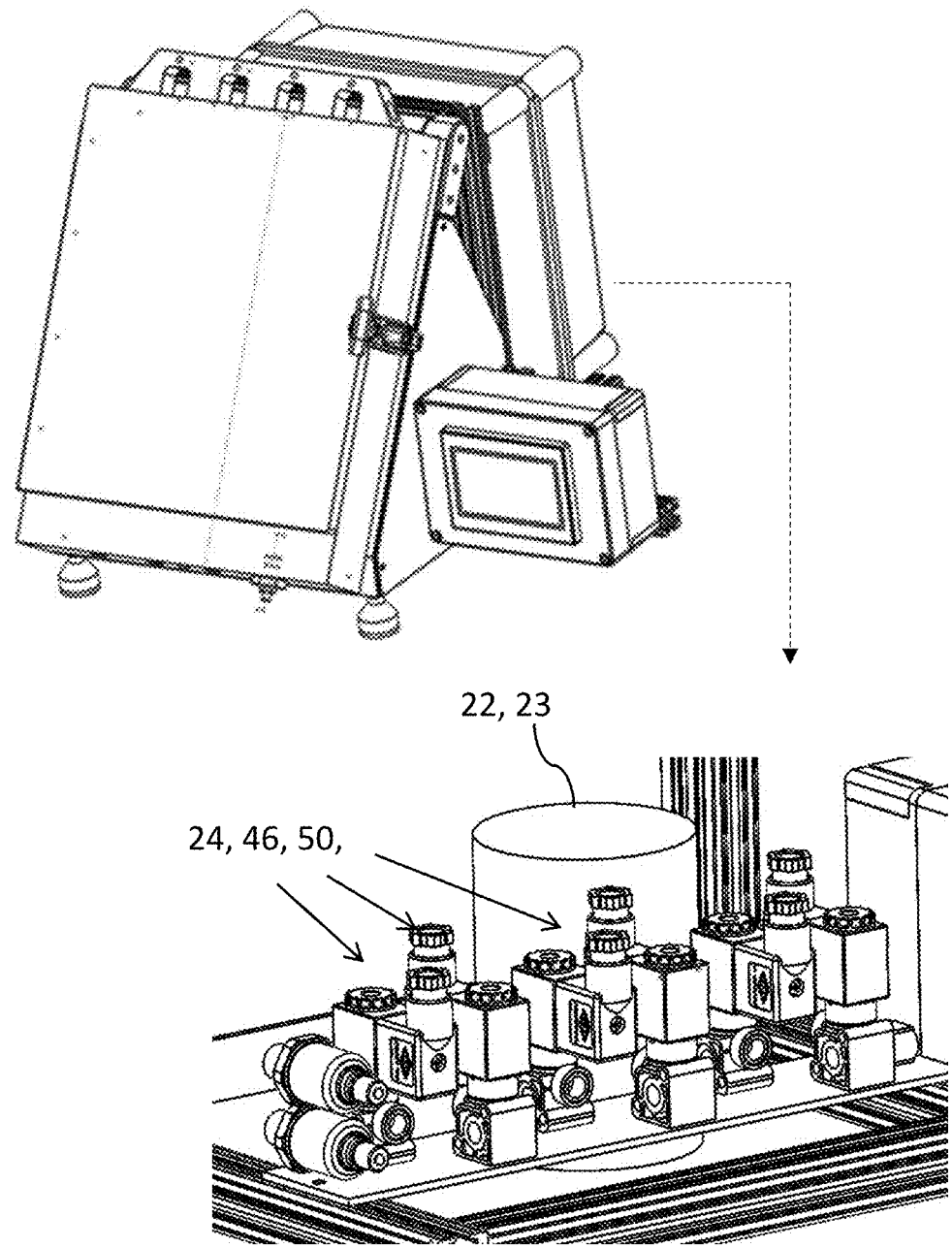
FIG. 7 depicts an arrangement of in-line valves 24, 46, 50 and vacuum pump/tank 22, 23.
Figure 8:
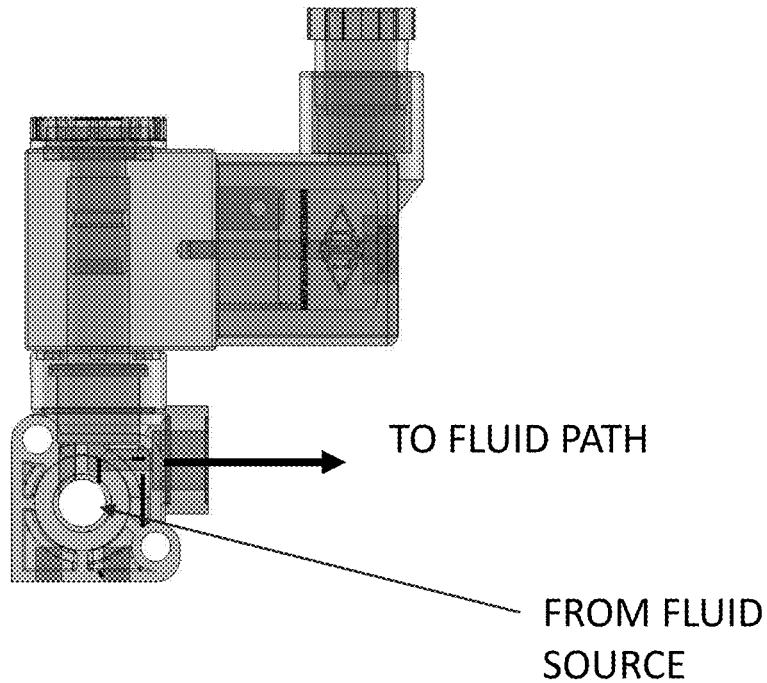
FIG. 8 depicts an exemplary 3-way valve.
Figure 8:
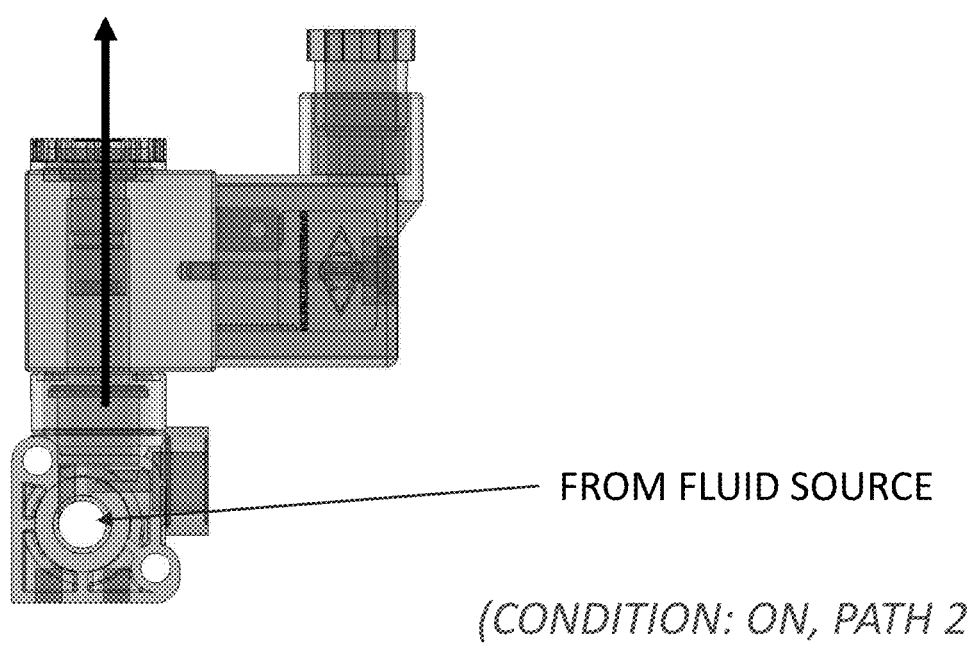

As shown more clearly in FIGS. 4 and 7, the receiving chamber 12 is configured to seal air-tight, such that the pressure within the chamber 12 can be regulated by way of a vacuum pump 22 or vacuum tank 23 and chamber vacuum valve 24. Hereinafter, the term "vacuum pump" is intended to alternatively encompass a vacuum tank under vacuum. Returning to FIG. 3, An air-tight seal can be accomplished by providing a chamber door 26 that closes against a suitable gasket 28, which is typically a ring of rubber other material that seals the juncture between two surfaces air-tight.

As shown more clearly in FIG. 3, the fitting train 20 regulates passage of liquid into the receiving chamber 12 and thus into a mounted container 14 for filling. The fitting train 20 is in fluid communication with a feed line 30 to deliver a liquid, such as a medication. By "fluid communication" it is meant that the fitting train 20 and feed line 30 are connected in such a way that a liquid can pass from one component to another.

In preferred embodiments, the container 14 is mounted to the train 20 by mating the container 14 to a first valve 32, which is itself is mated or able to be mated to a second valve 34 to form a pair of valves 32, 34. Examples of suitable valves include a variety of mechanical valves used in the medical device arts. In some embodiments, at least one valve 32, 34 is a luer valve or a spike valve.

Preferably, one of the valves 32, 34 within the pair of valves 32, 34 controls the opening and closing of both valves 32, 34 within the pair of valves 32, 34. Exemplary embodiments of valve combinations that can be used include valves disclosed in U.S. Pat. No. 6,745,998 by Doyle, U.S. Pat. No. 8,647,310 by Fangrow et al., U.S. Pat. No. 9,849,277 by Stroup, U.S. Pat. No. 10,299,993 by Stroup, and others. Most preferably, as shown in FIG. 3, a first valve 32, which connects to the container 14, is able to open both the first and second valves 32, 34 by rotating the first valve 32 in a first direction, and close both the first valve 32 and second valve 34 by rotating the first valve 32 in the opposite direction. Preferably, rotation of the container 14 rotates the first valve 32.

Figure 5:
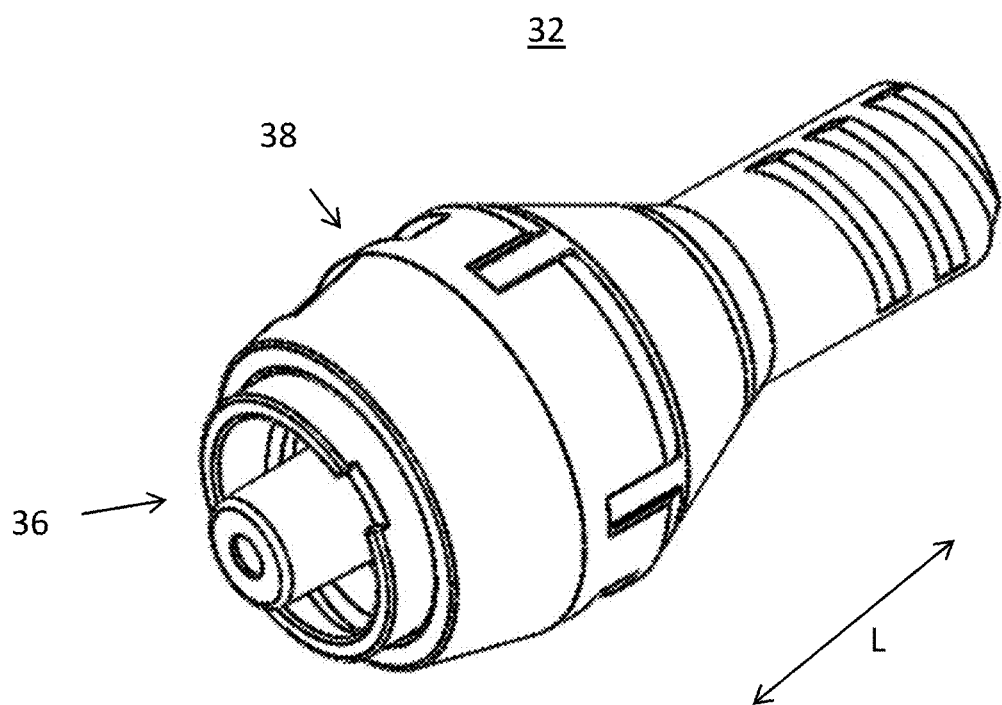
FIG. 5 depicts an exemplary valve 32 with inner housing 36 that moves longitudinally L relative to an outer housing 38 for valve operation.
Figure 6:
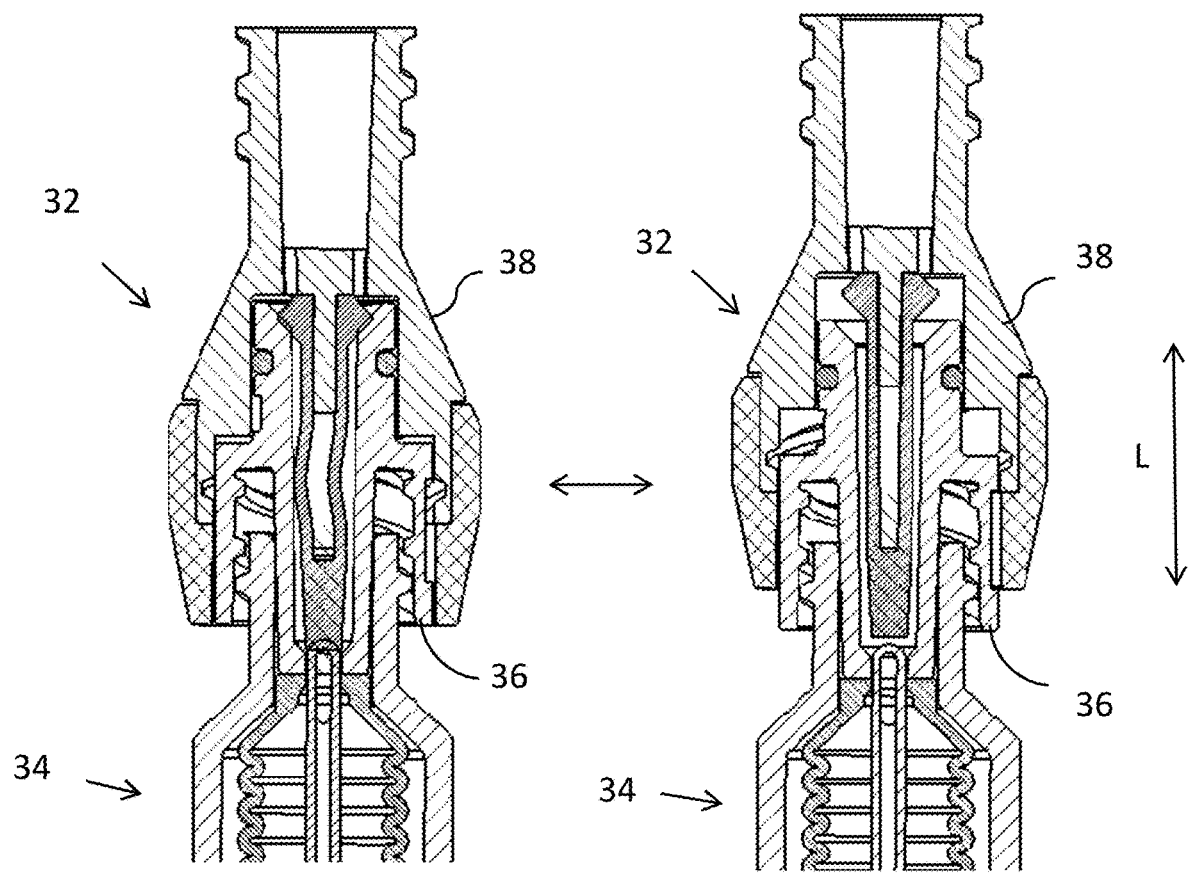
FIG. 6 depicts the opening of a pair of valves 32, 34 by a single valve 32.

An exemplary valve configuration is shown in FIGS. 5-6, where a first valve 32 has an inner housing 36 configured for longitudinal L movement with respect to an outer housing 38. More specifically, the pair of valves 32, 34 are joined by rotating the first valve 32 in a first direction. Continuing rotation opens the second valve 34, such as by displacing a spike while locking the two valves 32, 34 together or rotation of a barrier within the second valve 34. Still further rotation in a same direction causes longitudinal L movement of the inner housing 36, which opens the first valve 32. That is, the longitudinal L movement occurs by continued rotation of the first valve 32 along a rationally fixed second valve 34. In the preferred configuration, the second valve 34 opens before the first valve 32. After the container 14 is filled, closing the valve pair 32, 34 is by way of rotating the first valve 32 in the opposite direction, which causes the inner housing 36 to retreat longitudinally L thereby closing the first valve 32, followed by closing the second valve 34. Upon closure, the container 14, together with the first valve 32 can be removed and thus detached from the second valve 34. When detached, both valves 32, 34 are in a closed position.

Returning to FIG. 3, the fitting train 20 is mounted to the chamber 12 by traversing a throughbore. Maintaining the air-tight seal is accomplished by a bung 40 with tapped channel, which is connected to the second valve 34 and feed line 30 by way of suitable national pipe thread (NPT) to luer connectors 42.

Referring to FIGS. 1-8 collectively, operation of the system 10 begins by connecting the feed line 30 to a feed tank 44, which houses the liquid to be delivered. In such an instance, a feed valve 46 is preferably closed. The containers 14, in this example syringes 15, in need of filling are preferably attached to the fitting train 20, such as by locking each syringe 15 to its own first valve 32 and locking the first valve 32 to the second valve 34. Both valves 32, 34 are opened. The chamber door 26 is closed to seal the chamber 12. As introduced above, a user can enter information into the control module 18 regarding the number and volume of syringes 15 to be filled or can enter any other data desired, such as, but not limited to liquid contents or medication identifiers, liquid concentration, administration instructions, patient identifiers, and patient treatment information.

The container 14 filling operation is then executed. The syringe 15 filling operation is performed by computer software, preferably loaded in the control module 18. Filling begins by inducing a vacuum in the chamber 12. This can be accomplished by opening a chamber vacuum valve 24 that functionally connects the chamber 12 interior to a vacuum pump 22 through a vacuum line 48. Next, a vacuum is induced in the feed line 30, such as by opening a feed line vacuum valve 50 that functionally connects the feed line 30 and thus syringe 15 interior to a same or different vacuum pump 22. Afterwards, the feed line vacuum valve 50 is closed to hold the vacuum in the feed line 30 and thus the syringe 15. Opening the feed valve 46 permits the vacuum forces to feed liquid from the feed tank 44, through the feed line 30 and into the syringes 15 to permit filling. After the syringes 15 are filled, the control module 18 instructs the feed valve 46 to close, thereby halting further delivery of liquid to the fitting train 20. The artisan will appreciate that the vacuum based system may also include one or more vacuum meters 52 to monitor the vacuum.

When filling syringes 15 with liquid, in some embodiments, the filling can continue until the syringe plunger abuts the chamber wall or a chamber barrier. In alternative embodiments, the control module 18 is preprogrammed with a run time, which shuts off the feed valve 46 upon expiration of the run time. In still other embodiments a flow meter is positioned along the feed line 30 to measure the volume of passing liquid, which updates the control module 18 and thus permits comparison against a preprogrammed flow volume threshold, and thus provides an indicator when to initiate a close signal to the feed valve 46.

After filling the containers is complete, the control module instructs the feed valve 46 to close, to prevent further flow of liquid. The chamber vacuum valve 24 (preferably a 3-way valve) is purged to atmosphere, thereby permitting the chamber door 26 to be opened and the filled syringe(s) 15 removed.

Figure 9:
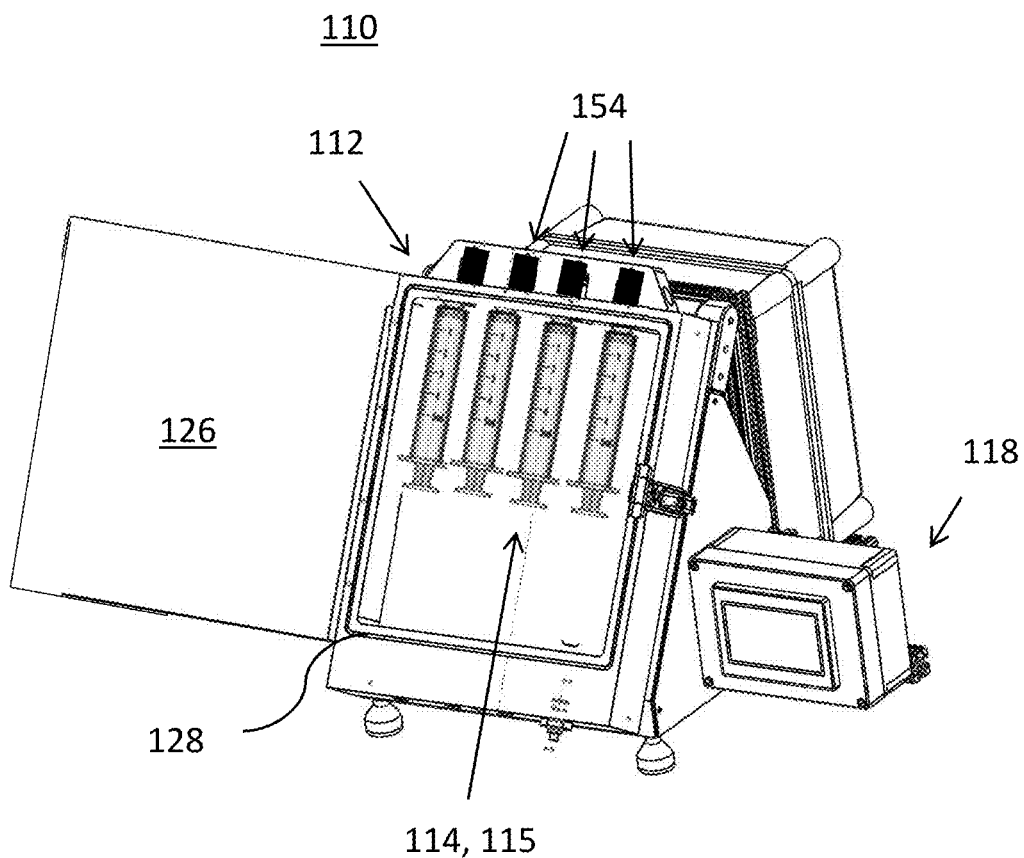
FIG. 9 depicts another exemplary vacuum-controlled liquid delivery system 110.
Figure 10:
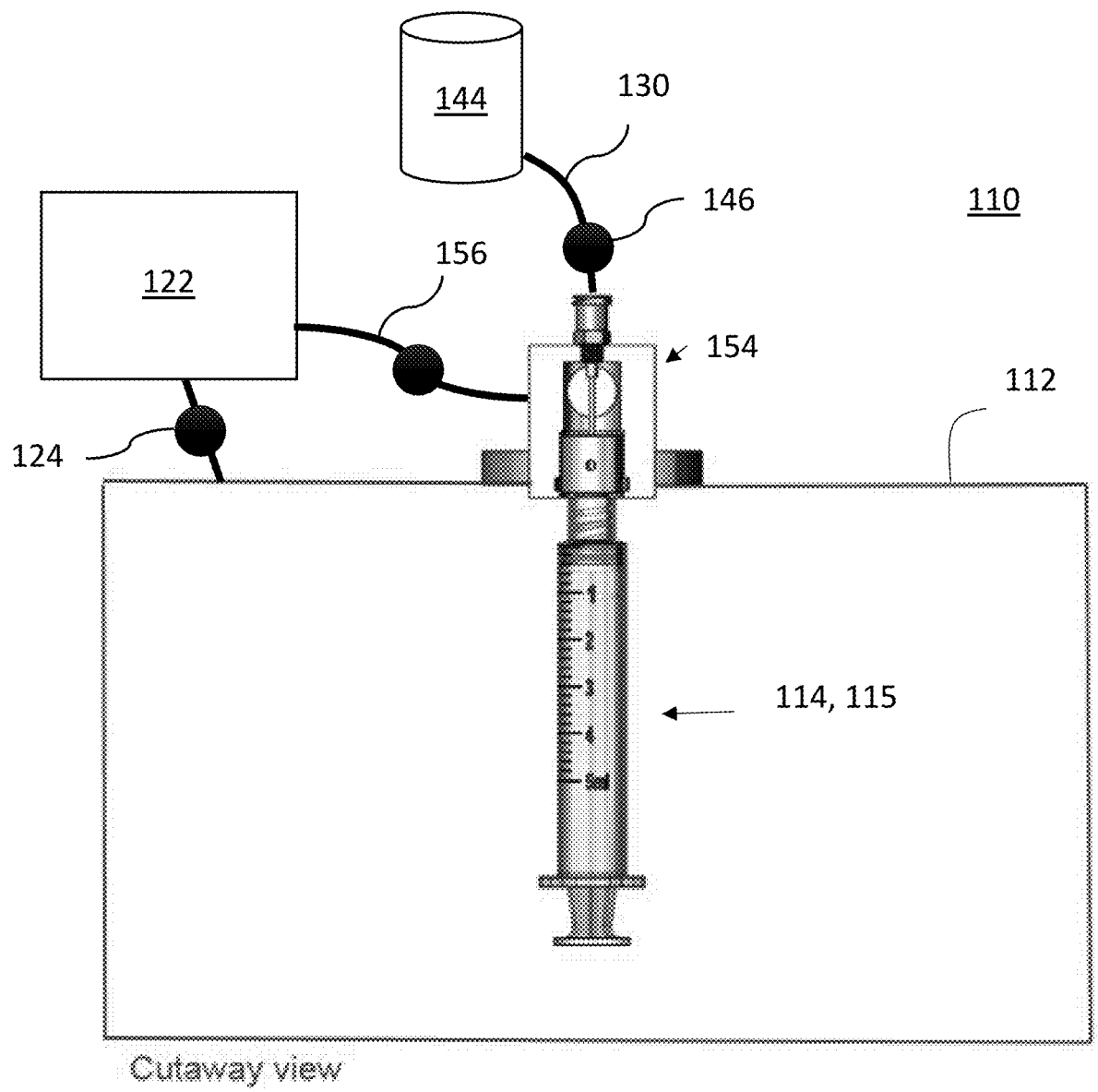
FIG. 10 depicts the attachment of a capped syringe 115 to a manifold assembly 154 for receiving liquid medication.

FIGS. 9-10 depict another exemplary embodiment of a vacuum controlled liquid delivery system 110. The system 110 includes a receiving chamber 112 sized to house a container 114 during its expansion, in particular, during filling. Similarly, the receiving chamber 112 is configured to seal air-tight. In some embodiments, the receiving chamber 112 houses one or more syringes 115. In other embodiments, the receiving chamber 112 houses one or more expandable bags (not shown). Again, while syringes 115 are typically expandable by way of a movable plunger, expandable bags are typically expandable by unfolding. The artisan will appreciate that syringes 115 can be of any volume, such as, but not limited to less than 1 mL, 1 mL, 5 mL, 10 mL, 25 mL, 50 mL, and more than 50 mL. Though nonlimiting, containers 114 greater than about 100 mL are more frequently provided in the form of an expandable bag, akin to IV bags used during medical treatment. One of ordinary skill in the art will appreciate that, like the syringes 115 bags can be of any size, such as, but not limited to less than 50 mL, 100 mL, 250 mL, 500 mL, 1000 mL, and more than 1000 mL. Thus, the dimensions of the receiving chamber 112 can vary depending on the size and number of containers 114 that are to be filled with the liquid.

In view of the above, FIG. 9 depicts an exemplary delivery system 110 with four syringes 115 added for filling with a medication. While four syringes 115 are shown, the system 110 can be configured for delivering liquid to as few as one syringe 115 and by altering the size of the chamber 112 many more than four syringes 115

Likewise, in some embodiments the user inputs the number and volume of containers 114 into the control module 118 In other embodiments, inserting containers 114 into the manifold 154 detects the presence of the container 114, such as by an optical detector (not shown), and notifies the control module 118 to prompt the use for any additional information needed or desired. Accordingly, in some embodiments, the user may be prompted to enter or confirm a container 114 volume and/or configuration. Naturally, technologies such as bar code readers could be adapted to enter and communicate information about the particular container 114 and liquid.

Figure 11:
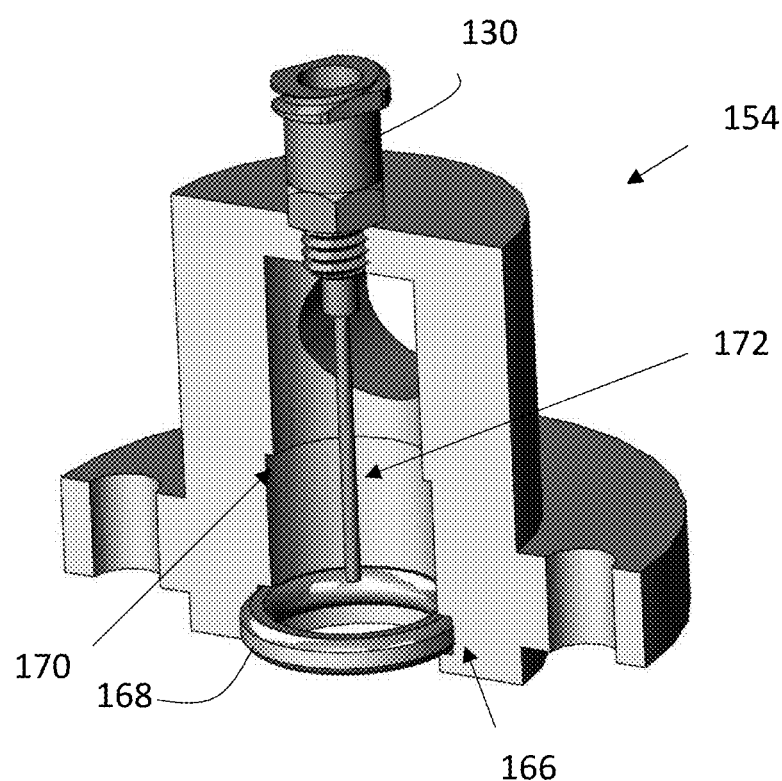
FIG. 11 depicts an exemplary manifold assembly 154.

Show more clearly in FIGS. 9-11 collectively, the receiving chamber 112 is configured to seal air-tight, such that the pressure within the chamber 112 can be regulated by way of a vacuum pump 122 and chamber vacuum valve 124. As with other embodiments, the term "vacuum pump" as used herein is also intended to encompass a vacuum tank under vacuum. An air-tight seal can be accomplished by providing a chamber door 126 that closes against a suitable gasket 128, which is typically a ring of rubber other material that seals the juncture between two surfaces air-tight. Thus, the receiving chamber 112 acts as housing for the expandable container 114 (e.g. syringe 115, expandable bag) during liquid delivery and also acts as a vacuum chamber, which decreases in pressure to affect liquid delivery into the expandable container 114 (e.g. syringe 115, expandable bag). In particular, the generated pressure difference expands the container 114, such as pulling a syringe plunger outward or opening a collapsed bag, which draws liquid into the syringe 15 or bag for filling.

The system 110 also includes a manifold assembly 154 having a feed line 130 and a manifold vacuum line 156. The feed line 130 is configured to feed or deliver liquid, and the manifold vacuum line 156 is functionally coupled to a vacuum pump 122 to regulate a vacuum within the manifold assembly 154.

The system 110 also includes a cap 160 configured to reversible engage the manifold assembly 154 at one end and reversibly cap an expandable container 114 (e.g. a syringe 115, expandable bag) at another end. The cap 160 has a septum 162 and a porous plug 164. As shown more clearly in FIGS. 13-14, when the cap 160 is attached to the manifold assembly 154, the feed line 130 passes through the septum 162 to access the interior of the cap 160 and thus the interior of a capped container 114 (e.g. syringe 115, expandable bag). During liquid delivery, the porous plug 164 contacts the liquid, which seals the cap 160 from the manifold assembly 154. Thus, the manifold assembly 154 is configured to engage a capped container 114 and direct entry of a feed line 130 through the cap 160 to access the container 114 for filling. By "configured to engage a capped container" it is meant that the cap 160 and manifold assembly 154 are joined to form an air-tight seal. As such, the manifold assembly 154 can engage the cap 160 using any suitable mechanism that permits an air-tight seal. In some embodiment, the cap 160 and manifold assembly 154 have complementary engaging structures that form the air-tight seal. In some embodiments the cap 160 and manifold assembly 154 have a twist lock connection that forms the air-tight seal. In still other embodiments, the cap 160 and manifold assembly 154 use friction fit engagement. Still further, as shown more clearly in FIG. 11, the manifold assembly 154 may be partially slotted 166 for seating of an O-ring 168, which forms the air-tight seal with the cap 160. In some embodiments, the cap 160 is inserted into the manifold assembly 154, until reaching an inner stop 170, which limits the depth of insertion.

Returning to FIGS. 12 and 13, the feed line 130 can be directed through the septum 162 of the cap 160 during engagement or after engagement. If directed during engagement, the feed line 130 can remain stationary while the cap 160 is raised towards the feed line 130, which permits piercing of the septum 162. If directed after engagement, the cap 160 can be fully engaged, then the feed line 130 mechanically pressed towards and through the cap 160.

Referring to FIGS. 10-13, the feed line 130 transfers liquid into the expandable container 114 (e.g. syringe 115, expandable bag) for filling. As such, one end the feed line 130 is adapted for connection with a feed tank 144, such as liquid reservoir that houses medication. At another end, preferably the feed line 130 has a non-coring needle 172 for passing through the septum 162. Non-coring needles 172 and septums 162 for use with non-coring needles 172 that are well known in the art can be adapted for use with the systems 110 and methods herein. As a nonlimiting example, a non-coring needle 172 can be used with a silicone septum 162 or a polymer based septum 162. Thus, during operation, a feed line 130 fluidly connected to a liquid reservoir 144 delivers the liquid across the septum 162 of the cap 160 and into an engaged container 114 (e.g. syringe 115 or expandable bag) due to the pressure difference formed in the chamber 112. When disengaged, the septum 162 maintains a fluid tight seal. The feed line 130 can also include a feed valve 146 to regulate the flow of liquid through the feed line 130.

The cap 160 is configured for coupling with the container 114 at one end and engagement with the manifold assembly 154 at another end. In embodiments where the container 114 is a syringe 115, the cap 160 coupling is preferably a Luer fitting. In embodiments where the container 114 is an expandable bag, the cap 160 coupling can be any suitable male or female coupling configured for use with the expandable bag.

When the cap 160 is fully engaged the porous plug 164 is exposed to both the interior of the manifold assembly 154 and the interior of the cap 160. Thus, the porous plug 164 regulates communication between the interior of the manifold assembly 154 and the interior of the cap 160. Accordingly, upon engagement of the cap 160 or capped syringe 115 with the manifold assembly 152, air pressure is equalized across the cap 160 and manifold assembly 154 through the plug 164. To this end, air can be evacuated from the cap 160 and container 114 (e.g. syringe 115, expandable bag) by evacuating air from the manifold assembly 154, such as by applying a vacuum. Reducing pressure within the manifold assembly 154 to evacuate air is performed through the manifold vacuum line 156. That is, the manifold vacuum line 156 is used to substantially evacuate air from the manifold assembly 154 and thus inside the cap 160 and container 114 (e.g. syringe 115, expandable bag).

Like managing the internal pressure of the chamber 112, adjusting pressure within the manifold assembly 154 can be performed using a variety of vacuum pumps 122 known in the industry. Procedurally, the vacuum is typically applied after engagement of the capped container 114 (e.g. syringe 115, expandable bag) to evacuate air from the interior of the cap 160 and expandable container 114 (e.g. syringe 115, expandable bag). After filling the container 114 (e.g. syringe 115, expandable bag), the vacuum can be released to permit the interior of the manifold assembly 154 to return to ambient or atmospheric pressure. Ambient or atmospheric pressure is typically desired when engaging and disengaging a capped syringe 115.

As already introduced, the porous plug 164 modulates the communication between the interior of the cap 160 and the manifold assembly 154. When open, the interior of the cap 160 equilibrates with the interior of the manifold assembly 154. When closed, the cap 160 interior and interior of the manifold assembly 154 are isolated from one another. The porous plug 164 begins in an open configuration but closes in response to the presence of liquid. That is, the porous plug 164 closes and becomes air-tight and liquid-tight when exposed to liquid.

Figure 12:
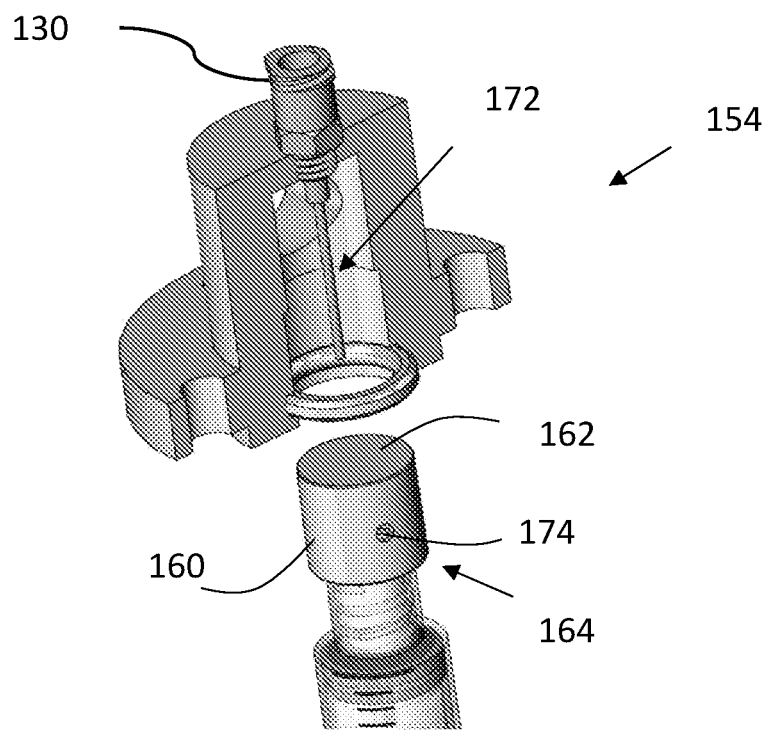
FIGS. 12-13 depict the interaction between cap 160 and manifold assembly 154.
Figure 13:
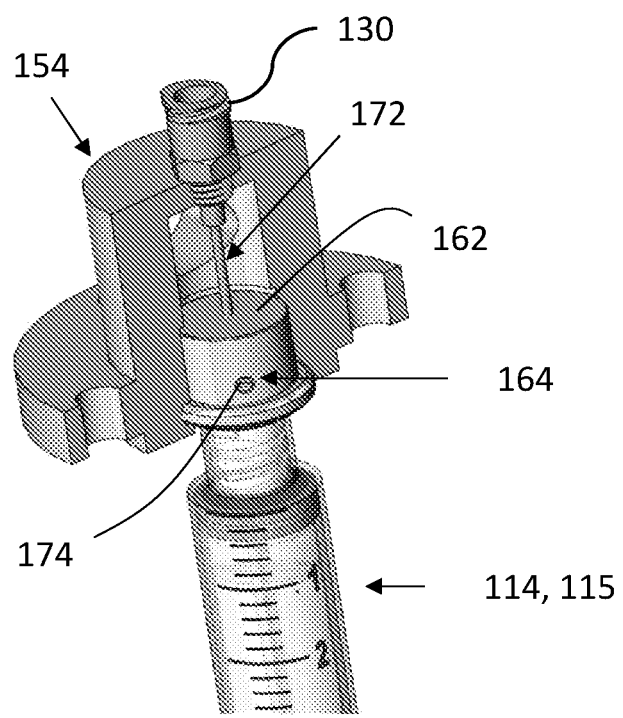

Shown more clearly in FIGS. 12-13, preferably, the porous plug 164 includes an aperture 174 and a swellable matrix that swells to seal the aperture 174 when contacting liquid. The aperture 174 can be a plurality of apertures 174 or a single aperture 174. Further, the one or more apertures 174 can vary in size depending on the desired configuration. As nonlimiting guidance, the aperture 174 can be from a few microns to a few millimeters, such as 250 μm, 500 μm, 1 mm, 2 mm, 3 mm or more. The swellable matrix can be a porous membrane that closes upon contact with liquid. In some embodiments the porous plug 164 includes a sucrose material that swells to seal the aperture 174 when contacting liquid. In other embodiments, the porous plug 164 includes a hydrogel that swells to seal the aperture 174 when contacting liquid. In other embodiments, the porous plug 164 includes polymer that swells or polymerizes to seal the aperture 174 when contacting liquid.

Turning now to FIGS. 9-14, another exemplary method of delivering a liquid to a container 114 (depicted as a syringe 115) is demonstrated, which includes providing a vacuum controlled liquid delivery system 110 as described. If not already installed, the feed line 130 is connected at one end to a feed tank 122 and at the other end, which preferably includes a non-coring needle 172, to the manifold assembly 154. A syringe 115 is capped. The capped syringe 115 is inserted into the manifold assembly 154 by way of the receiving chamber 112.

The manifold assembly 154 forms an air-tight seal with the cap 160, due the O-ring 168, and the porous plug 164 equalizes pressure between the interior of the manifold assembly 154 and the interior of the cap 160. Air is evacuated from the chamber 112, and a constant vacuum pressure is maintained. Vacuum is applied through the manifold vacuum line 156 to evacuate air from the manifold assembly 154 and cap 160. Feed valve 146 is opened, and liquid is drawn through the feed line 130 and into the syringe 115 due to the vacuum within the chamber 112 and manifold assembly 154, thereby filling the syringe 115. Filling the syringe 115 results in contact between the porous plug 164 and the liquid, which swells the porous plug 164 to isolate the cap 160 interior from the interior of the manifold assembly 154, thereby preventing the liquid from permeating into the manifold assembly 112. When filling syringes 115 with liquid, in some embodiments, the filling can continue until the syringe plunger abuts the chamber wall or a chamber barrier. In alternative embodiments, the control module 18 is preprogrammed with a run time, which shuts off the feed valve 130 upon expiration of the run time. In still other embodiments a flow meter is positioned along the feed line 130 to measure the volume of passing liquid, which updates the control module 118 and thus permits comparison against a preprogrammed flow volume threshold, and thus provides an indicator when to initiate a close signal to the feed valve 146.

Figure 14:
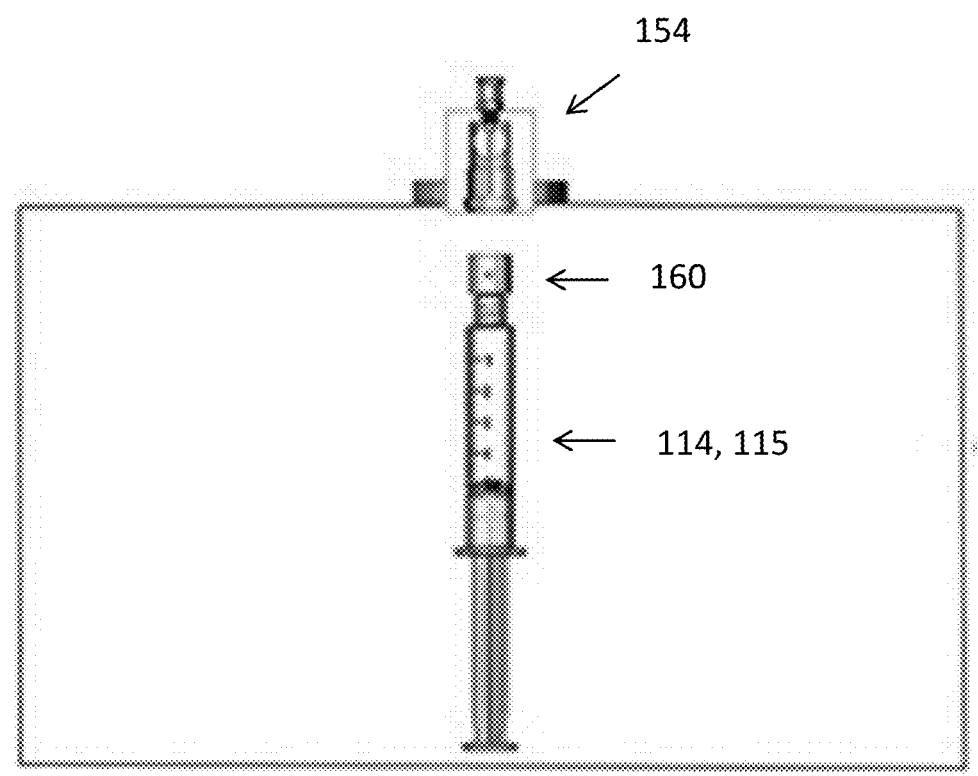
FIG. 14 depicts a filled syringe 115 removed from the manifold assembly 154.

Once the syringe 115 is filled, the feed line 130 is the obstructed, such as by closing the feed valve 146. The vacuum from both manifold assembly 154 and chamber 112 is released to permit each to return to atmospheric pressure and as shown in FIG. 14, the filled syringe 115 is disengaged from the manifold assembly 154.

The invention described in the above exemplary embodiments, may be embodied in other specific forms without departing from the spirit or essential characteristics thereof. The specific embodiments previously described are therefor to be considered as illustrative of, and not limiting, the scope of the invention.

What is claimed is:

1. A vacuum controlled liquid delivery system, comprising:
    a) a receiving chamber sized to house an expandable container during its expansion, the receiving chamber configured to seal air-tight;
    b) a manifold assembly accessing an interior of the chamber, the manifold assembly comprising a feed line and a manifold vacuum line, wherein the feed line is configured to feed liquid, and the manifold vacuum line is functionally coupled to a vacuum pump to regulate a vacuum within the manifold assembly;
    c) a cap configured to reversibly engage the manifold assembly to form an air-tight seal and configured to cap an expandable container, the cap comprising a septum and a porous plug, wherein when the cap is attached to the manifold assembly the feed line passes through the septum to permit passage of liquid and further wherein the porous plug seals upon contact with liquid.

2. The liquid delivery system of claim 1, wherein pressure within receiving chamber is regulated by a chamber vacuum valve and a same or different vacuum pump.

3. The system of claim 1, wherein the chamber comprises a barrier in alignment but spaced from the manifold assembly to limit expansion of an expanding container.

4. The system of claim 1, wherein the feed line comprises a non-coring needle for passage through the septum.

5. The system of claim 1, wherein the feed line comprises a feed valve that regulates the flow of liquid through the feed line.

6. The system of claim 1, wherein when the cap is fully engaged the porous plug is exposed to an interior of the manifold assembly and an interior of the cap, thereby regulating communication between the interior of the manifold assembly and the interior of the cap.

7. The system of claim 1, wherein the porous plug comprises an aperture and a swellable matrix that swells to seal the plug when contacting liquid.

8. The system of claim 7, wherein the swellable matrix comprises sucrose or a hydrogel.

9. A vacuum controlled liquid delivery method for filling a container, the method comprising:
   a) connecting the feed line of the system of claim 1 to a feed tank comprising a liquid for delivery;
   b) capping a collapsible container with the cap;
   c) engaging the capped container with the manifold assembly such that an interior of the cap forms an air-tight seal with an interior of the manifold assembly, and the fluid line passes through the septum to fluidly access the container;
   d) inducing a vacuum in the receiving chamber and in the manifold assembly to position the container in a compressed state under vacuum forces;
   e) unsealing the fluid feed line to feed the liquid into the container under vacuum and against the porous plug, thereby sealing the plug;
   f) resealing the feed line to obstruct flow through the feed line;
   g) relieving the vacuum from the receiving chamber and the manifold assembly; and
   h) disengaging the capped syringe from the manifold assembly.

* * * * *